United States Patent
Brown, III

(10) Patent No.: US 6,409,651 B1
(45) Date of Patent: Jun. 25, 2002

(54) DEVICE FOR INTRAVASCULAR DELIVERY OF BETA EMITTING ISOTOPES

(75) Inventor: Charles L. Brown, III, Atlanta, GA (US)

(73) Assignee: GMP/Vascular, Inc., Fort Lauderdale, FL (US)

( * ) Notice: Subject to any disclaimer, the term of this patent is extended or adjusted under 35 U.S.C. 154(b) by 0 days.

(21) Appl. No.: 09/530,899
(22) PCT Filed: Nov. 6, 1998
(86) PCT No.: PCT/US98/23675
§ 371 (c)(1), (2), (4) Date: Jul. 13, 2000
(87) PCT Pub. No.: WO99/24117
PCT Pub. Date: May 20, 1999

Related U.S. Application Data

(60) Provisional application No. 60/064,611, filed on Nov. 7, 1997, provisional application No. 60/080,052, filed on Mar. 31, 1998, and provisional application No. 60/087,202, filed on May 29, 1998.

(51) Int. Cl.⁷ .................................................. A61N 5/00
(52) U.S. Cl. ............................................................ 600/3
(58) Field of Search ............................... 600/1, 2, 3, 4, 600/5, 6, 7, 8; 604/93, 96

(56) References Cited

U.S. PATENT DOCUMENTS

| | | |
|---|---|---|
| 5,199,939 A | 4/1993 | Dake et al. |
| 5,213,561 A | 5/1993 | Weinstein et al. |
| 5,302,168 A | 4/1994 | Hess |
| 5,484,384 A * | 1/1996 | Fearnot ......................... 600/3 |
| 5,498,227 A | 3/1996 | Mawad |
| 5,503,613 A | 4/1996 | Weinberger |
| 5,540,659 A | 7/1996 | Teirstein |
| 5,605,530 A | 2/1997 | Fischell et al. |
| 5,616,114 A | 4/1997 | Thornton et al. |
| 5,618,266 A | 4/1997 | Liprie |
| 5,643,171 A | 7/1997 | Bradshaw et al. |
| 5,662,580 A | 9/1997 | Bradshaw et al. |
| 5,683,345 A | 11/1997 | Waksman et al. |
| 5,707,332 A | 1/1998 | Weinberger |
| 5,782,740 A | 7/1998 | Schneiderman |
| 5,782,742 A | 7/1998 | Crocker et al. |
| 5,797,948 A | 8/1998 | Dunham |
| 5,833,593 A | 11/1998 | Liprie |
| 5,851,171 A | 12/1998 | Gasson |
| 5,855,546 A | 1/1999 | Hastings et al. |
| 5,865,720 A | 2/1999 | Hastings et al. |
| 5,879,282 A | 3/1999 | Fischell et al. |
| 5,882,290 A | 3/1999 | Kume |
| 5,891,091 A | 4/1999 | Teirstein |
| 5,899,882 A | 5/1999 | Waksman et al. |
| 5,910,101 A | 6/1999 | Andrews et al. |
| 5,916,143 A * | 6/1999 | Apple et al. .................... 600/3 |
| 5,924,974 A | 7/1999 | Loffler |
| 5,947,889 A | 9/1999 | Hehrlein |
| 5,971,909 A | 10/1999 | Bradshaw et al. |
| 5,976,106 A | 11/1999 | Verin et al. |
| 6,149,574 A * | 11/2000 | Trauthen et al. ................ 600/3 |
| 6,210,312 B1 * | 4/2001 | Nagy ............................. 600/3 |

* cited by examiner

Primary Examiner—Kevin Shaver
Assistant Examiner—Brian Szmal
(74) Attorney, Agent, or Firm—Sutherland Asbill & Brennan LLP

(57) ABSTRACT

The present invention provides a device (10), and methods of use thereof, for the targeted delivery of radiation, in vivo. The therapeutic radiation delivered by the device (10) of the present invention can be used, for example, to prevent restenosis after angioplasty. The catheter device (10) of the present invention is especially suited for such treatment because it substantially aids in the delivery of radiation to an intravascular treatment site. In addition, to delivering radiation emitting materials to an intravascular site, the present invention can also incorporate radiation shielding to increase the safety and accuracy of the delivery of the radiation emitting materials.

20 Claims, 2 Drawing Sheets

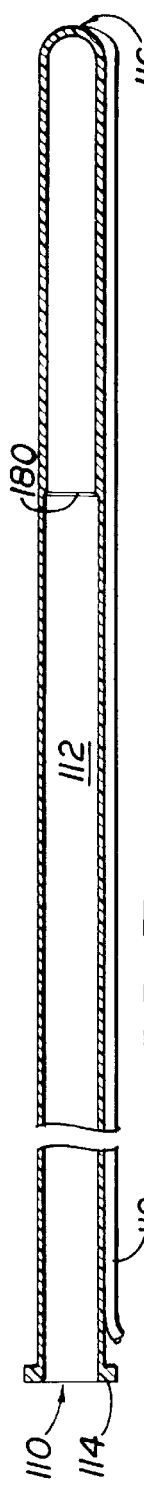
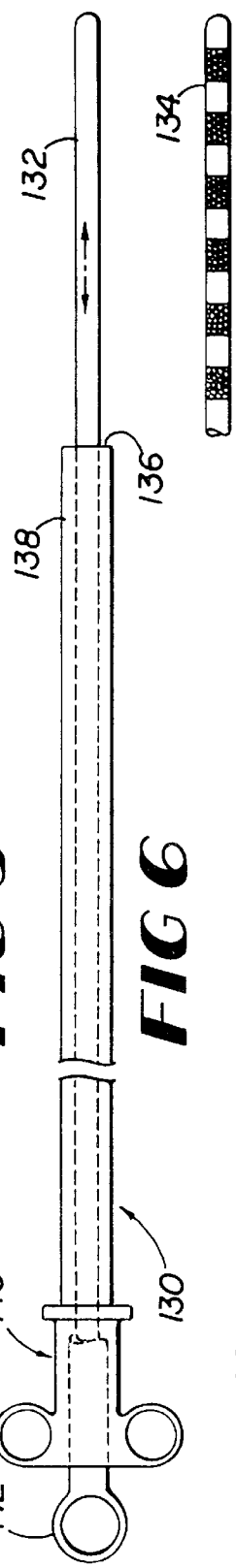
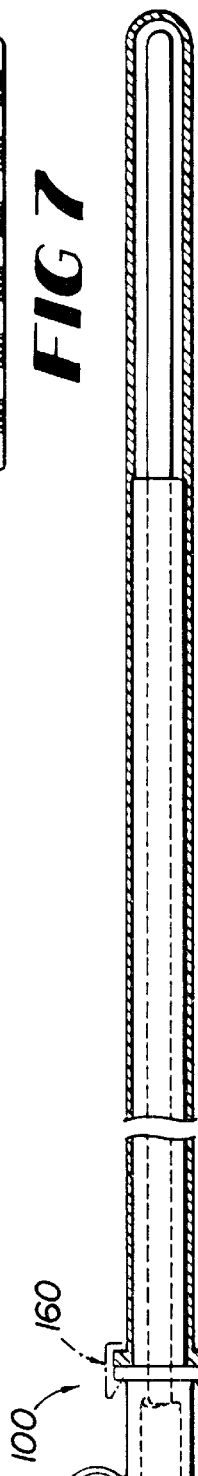
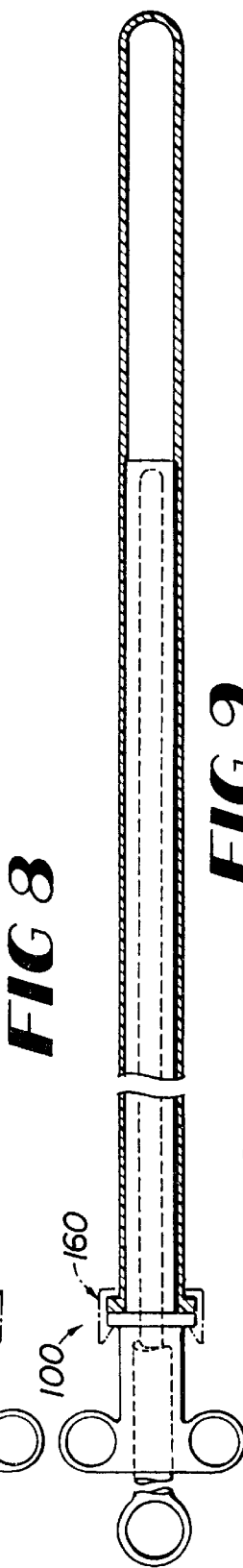
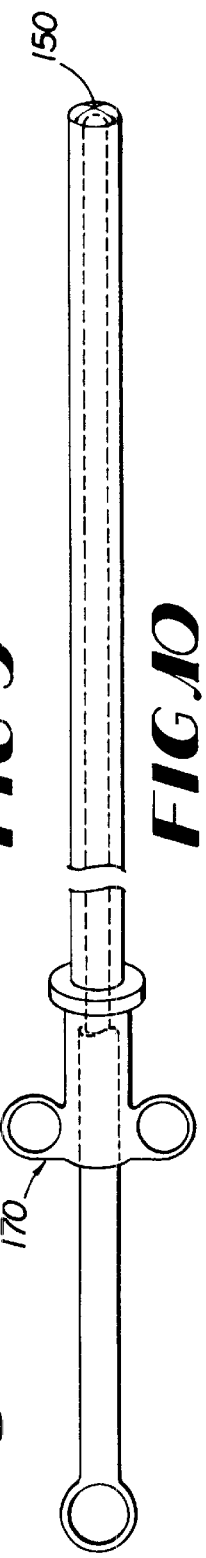
FIG 5
FIG 6
FIG 7
FIG 8
FIG 9
FIG 10

DEVICE FOR INTRAVASCULAR DELIVERY OF BETA EMITTING ISOTOPES

This patent application claims priority from U.S. Provisional Application No. 60/064,611, filed Nov. 7, 1997; U.S. Provisional Application No. 60/080,052, filed Mar. 31, 1998; and U.S. Provisional Application No. 60/087,202, filed May 29, 1998.

FIELD OF THE INVENTION

The present invention relates to catheters designed for delivery of therapeutic substances in vivo. More specifically, the present invention relates to catheters designed for intravascular delivery of therapeutic radiation in vivo.

BACKGROUND OF THE INVENTION

Isotopic radiation therapy has been proposed for the treatment of various vascular disorders, such as restenosis following angioplasty. Prior to the present invention, it was believed that gamma emitting isotopes would be useful for peripheral brachy therapy. However, the use of gamma emitting isotopes poses a great deal of logistical difficulty in safely delivering the isotope.

The use of beta emitting isotopes would be easier and safer for vascular brachy therapy because beta emitting isotopes have relatively low penetrance and are easier to shield. However, the use of beta emitting isotopes is limited by the penetrating depth, which is about 3–4 mm at the appropriate doses required for intervention. Many arteries are larger than 3–4 mm, for example measuring 5 to 7 mm in diameter in the superficial femoral artery and even larger in the aortoiliac system.

What is needed is a device for intravascular delivery which allows for the use of radiation emitting isotopes in larger diameter vessels, and which minimizes the safety precautions required by gamma emitting isotopes.

SUMMARY OF THE INVENTION

The present invention provides a device, and methods of use thereof, for the targeted delivery of radiation in vivo. The therapeutic radiation delivered by the device of the present invention can be used, for example, to prevent restenosis after angioplasty. The catheter of the present invention is especially suited for such treatment because it substantially aids in the delivery of radiation to an intravascular treatment site.

Further, the device of the present invention makes it possible for beta emitting isotopes to be used as sources of therapeutic radiation. The use of beta emitting isotopes is advantageous because they have low penetrance, e.g., in the range of 3–4 mm, and they are relatively easy to shield. Prior to the present invention, the low penetrance of the beta emitting isotopes has limited their usefulness in treating vascular sites because many vascular sites exceed in size the penetrance of beta emitting isotopes. By using the beta emitting isotopes in conjunction with the catheter of the present invention, this problem can be overcome by placing the beta emitting isotope at the vascular site. The present invention further overcomes this problem by placing the beta emitting isotopes in channels located on the periphery of an inflatable balloon connected to the end of the catheter. This balloon also increases the accuracy of the treatment delivery by immobilizing the catheter tip at the treatment site.

The present invention can also provide greater control over radiation delivery by providing a return channel for the radiation emitting isotopes rather than merely a blind port. Such a return channel allows for greater control of the treatment duration, as well as greater flexibility in dosing regimens. Further, the path of such return channels can also contribute to the radiation delivery.

The present invention allows delivery of isotopes via several methods. These include, but are not limited to, radioactive wires, radioactive seed trains, radioactive gases and liquids, as well as other radiation emitting materials known to one skilled in the art. Preferably, the present invention utilizes beta emitting isotopes, but other types of radiation emitting materials may be used and is contemplated as within the scope of the present invention. Examples of beta emitting isotopes used with the present invention are $^{90}$strontium, $^{125}$iodine, $^{192}$iridium, itrium, $^{188}$rhenium, $^{186}$rhenium and $^{133}$xenom.

In another embodiment of the present invention, the catheter can also include a radiation shielding. Such shielding is used to increase the accuracy and safety of the radiation delivery by preventing undesired radiation emission from the delivery channels. Further, radiation shielding can be used in the present invention to avoid the necessity of complex afterflow devices. For example, radiation emitting isotopes can be situated within radiation shielding inside the catheter. Once the catheter is in place, the radiation emitting isotopes can be exposed. This can be accomplished, alternatively, by moving the shielding or by moving the radiation emitting isotopes, such that the radiation emitting isotopes are no longer shielded.

The present invention can also take the form of a double catheter system. In this embodiment of the present invention, the inner, shielded catheter contains a movable radiation emitting source. The radiation emitting source can be, for example, an irradiated wire or a series of radiation emitting pellets embedded in a plastic wire matrix. The wire can be movable such that it can be extended beyond the distal end of the radiation shielding. The present invention also provides that this shielded catheter can have a radiation proof valve located on its distal tip. An outer catheter can contain two lumens: an eccentrically located guide wire lumen and a large lumen sized to receive the inner, shielded catheter. The shielded catheter can be inserted into the outer catheter prior to insertion of the catheter system in vivo. Once the catheter has been properly placed in vivo, the radiation emitting wire can be extended beyond the shielding to complete the delivery of the radiation to the treatment site.

Such a system can provide a number of advantages. For example, the outer catheter can be disposable. Additionally, the shielded catheter can be used to store the radiation emitting source between uses. Such a system also avoids the necessity of complex afterflow devices.

The present invention can also comprise a method of delivering radiation to an in vivo treatment site using a catheter. This method can comprise the steps of inserting the catheter until it is properly positioned in vivo; delivering the radiation emitting isotopes through the catheter or unshielding the radiation emitting source within the catheter; allowing the radiation treatment to continue for the appropriate amount of time; and then removing and/or reshielding the radiation emitting source.

Accordingly, it is an object of the present invention to provide catheters and methods that can safely and accurately deliver radiation emitting substances to a desired site.

It is another object of the present invention to provide catheters and methods that can safely and accurately deliver beta radiation emitting isotopes to a desired site.

It is another object of the present invention to provide a catheter and method that can be used to locally treat a diseased area using radiation.

It is another object of the present invention to provide a catheter and method that can be used to treat an intravascular site using radiation.

It is another object of the present invention to provide a catheter and method that can be used to treat restenosis.

It is another object of the present invention to provide a catheter and method that can be used to increase the therapeutic effectiveness of beta emitting isotopes by delivering them such that the distance between the beta emitting isotopes and the treatment site is less than the penetrance of the beta emitting isotopes.

It is another object of the present invention to provide a catheter and method that can be used to increase the effectiveness and safety of radiation therapy by utilizing radiation shielding.

These and other objects, features and advantages of the present invention will become apparent after a review of the following detailed description of the disclosed embodiments and the appended claims.

BRIEF DESCRIPTION OF THE DRAWINGS

FIG. 5 shows a catheter with a lumen capable of receiving a shielding catheter for use with the double catheter embodiment of the present invention.

FIG. 6 shows an embodiment of a shielding catheter with an active isotope wire extended for use with the double catheter embodiment of the present invention.

FIG. 7 shows an embodiment of a series of radiation emitting pellets embedded in a plastic wire matrix for use in a shielding catheter of the double catheter embodiment of the present invention.

FIG. 8 shows a double catheter embodiment with a shielding catheter secured by a locking mechanism within an outer catheter with an irradiated wire extended from the shielding catheter.

FIG. 9 shows a double catheter embodiment with a shielding catheter secured by a locking mechanism within an outer catheter with an irradiated wire contained within the shielding catheter.

FIG. 10 shows an embodiment of a shielding catheter having a locking mechanism to prevent the accidental depression of the syringe mechanism and having a radiation proof valve.

DETAILED DESCRIPTION OF THE PREFERRED EMBODIMENTS

The present invention provides a device, and methods of use thereof, for the targeted delivery of radiation in vivo. The therapeutic radiation delivered by the device of the present invention can be used, for example, to prevent restenosis after angioplasty. The catheter of the present invention is especially suited for such treatment because it substantially aids in the delivery of radiation to an intravascular treatment site.

Figure 1:
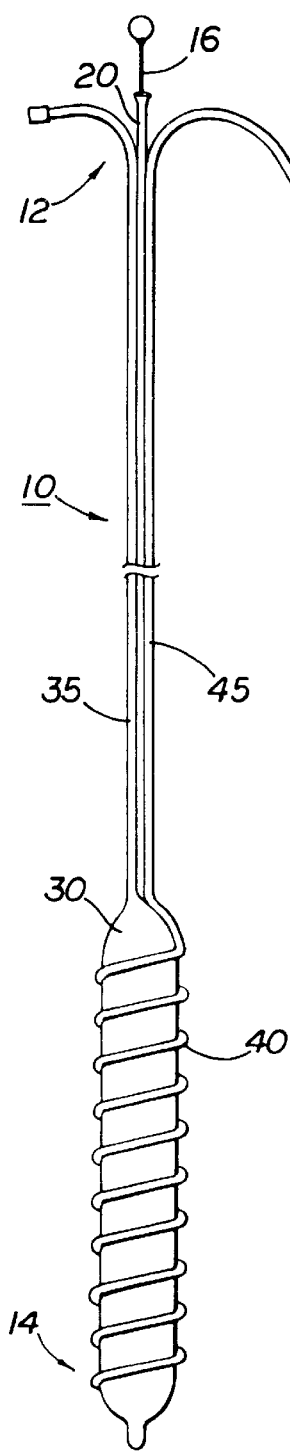
FIG. 1 shows an embodiment of a device for the delivery of radiation emitting isotopes of the present invention.

As shown in FIG. 1, the present invention can be embodied in a device 10, and methods of use thereof, for the intravascular delivery of radiation emitting isotopes. Beta emitting isotopes are preferred, however, any radiation emitting isotope can be used in the present invention. Uses of the device are not limited to any particular physical form of radioactive isotope, i.e. whether solid, liquid or gaseous. The device 10 has a proximal end 12 and a distal end 14. The device 10 comprises a central wire 16 containing lumen 20 used to direct the distal end 14 into position within a vascular cavity, e.g. an artery. The wire 16 can be left in place during operation, or removed, as the isotope is delivered peripherally as described below.

A central balloon 30 is inflated via an inflator channel 35 to secure the device 10 into position within the vascular cavity. A peripheral coil 40 is supplied with a therapeutic radiation emitting isotope via a delivery channel 45. The peripheral coil 40 is a stiff walled, closed-end channel wrapping the central balloon 30 in successive coils. In preferred embodiments, the balloon 30 can be about 10 mm with each loop of the peripheral coil 40 spaced about 1–2 mm apart. The isotope is delivered to the delivery channel 45 via an afterloader and sent into the vessel within the peripheral coil 40 surrounding the central balloon 30. After treatment, the isotope is retracted, the central balloon 30 is deflated and the device 10 is withdrawn from the vascular cavity.

Figure 2:
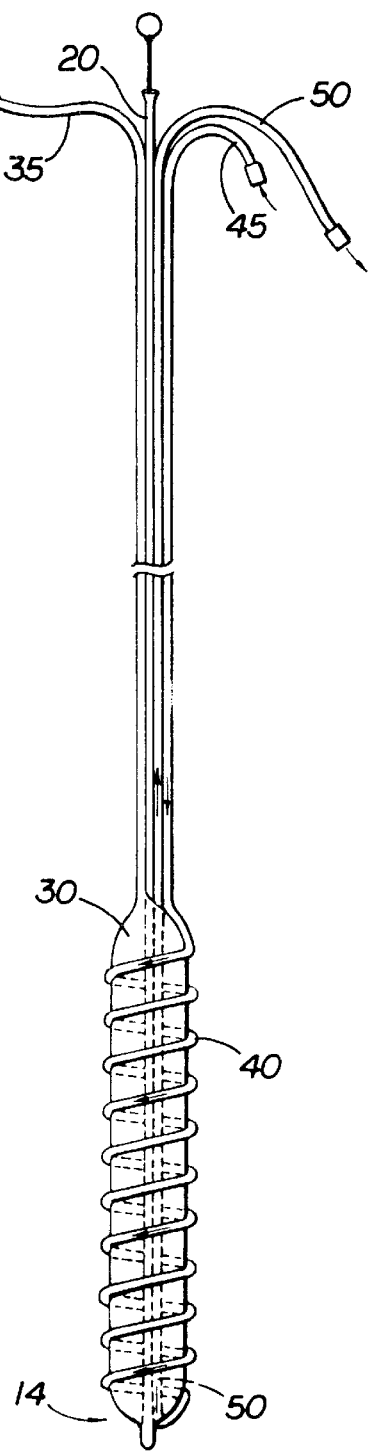
FIG. 2 shows an embodiment of a device for the delivery of radiation emitting isotopes including a centrally-located return channel.
Figure 3:
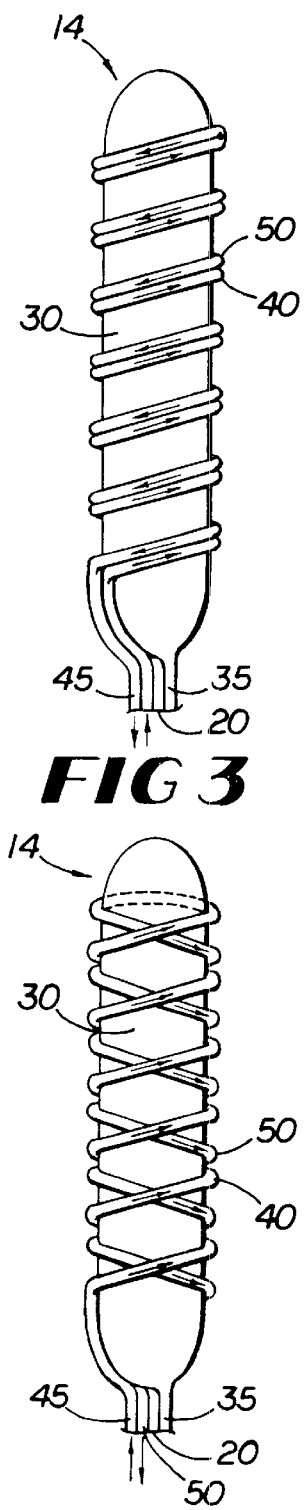
FIG. 3 shows an embodiment of a device for the delivery of radiation emitting isotopes including a return channel configured in a reverse parallel spiral relative to the peripheral coil.
Figure 4:
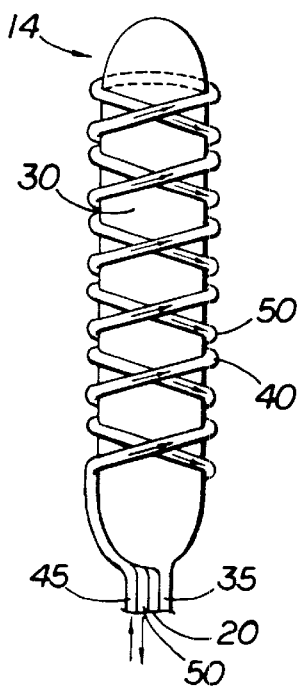
FIG. 4 shows an embodiment of a device for the delivery of radiation emitting isotopes including a return channel configured in a reverse helical design relative to the peripheral coil.

FIG. 2 shows another embodiment of the present invention. The peripheral coil 40 does not terminate in a "blind port" fashion, but instead is provided with a return lumen 50. This modification makes the delivery lumen "circular" in design. The return lumen 50 runs centrally as shown in FIG. 2, or, as shown in FIG. 3, can be configured in a reverse parallel spiral or, as shown in FIG. 4, can be configured in a reverse helical design. These embodiments allow a continuous loop for delivery of a liquid or gaseous substance, entering through one inflow delivery channel 45 and circling the balloon 30 with exit through the return lumen 50. The balloon design and central wire lumen design can be the same or different as in the first embodiment.

The present invention also contemplates that catheters containing optical fibers can be used for the delivery of electromagnetic radiation energy to the vessel walls. For example, the peripheral coil 40 can be supplied with such an optical fiber or bundle of fibers to emit therapeutic radiation via the delivery channel 45.

Furthermore, the present invention contemplates that catheters capable of emitting an electrical discharge can be used in conjunction with the device 10 for the therapeutic modulation of cell membranes. For example, the peripheral coil 40 and delivery channel 45 can be supplied with such an electrical catheter to emit therapeutic electrostimulation to the vascular cavity via the delivery channel 45. Alternatively, a separate lumen containing an electrical stimulator can be wrapped around the central balloon 30 in a parallel spiral with the peripheral coil 40, and thereby electrical charges can be administered to the vascular cavity along with the above-described isotopic or electromagnetic irradiation.

Further embodiments of the present invention also include radiation shielding to reduce unwanted irradiation. Embodiments including radiation shielding function to target radiation delivery by the manipulation of the relative positions of the radiation emitting materials and the radiation shielding. For example, a shielded radiation emitting material can be delivered to a desired location in vivo. Then, to effectuate delivery of radiation, the positions of the radiation emitting materials and the radiation shielding relative to each other can be altered such that the radiation emitting material is no longer shielded. The radiation shielding can be withdrawn, thereby unshielding the radiation emitting material; or, the radiation emitting material can be extended within the catheter beyond the radiation shielding.

The radiation shielding can be lead or one of several other materials such as various heavy metals. Other examples of radiation shielding material used in the present invention include tin, heavy plastic or other soft metals. Additionally, some of the embodiments of the present invention include radiation shielding in the form of a spiral coil in order to increase the flexibility of the radiation shielding. The choice of which material to use depends upon various factors such as thickness, cost, and flexibility and will vary depending upon the particular application, which is routinely determinable to one skilled in the art.

Such embodiments can further contain radiation proof valves. On the distal ends of the radiation shielded portions, such valves would reduce unwanted irradiation both prior to and after the catheter being placed in vivo. These valves provide radiation shielding while still allowing the radiation emitting material to selectively pass through them in both directions.

The movement of the radiation emitting material and/or the radiation shielding is achieved through various mechanisms. For example, a manually operated syringe mechanism can be used. In such a mechanism, a plunger is connected to the proximal end of the portion of the system to be moved, e.g. the radiation emitting material.

A preferred embodiment utilizing radiation shielding is shown in FIGS. 5–10. The radiation delivery system 100 is a two-part catheter system. The first part is a double lumen catheter 110. The larger central lumen 112 has an open proximal end 114 and a closed distal end 116. A second lumen 118 is eccentrically located and acts as the guide wire lumen. The system allows for the retraction of the wire from the delivery area after positioning of the catheter system 100. The second part of the delivery system 100 is a shielding catheter 130. The shielding catheter 130 houses the active isotope, for example, in the form of a wire 132. The active isotope wire 132 is a radiation emitting wire, as shown in FIG. 6, or a series of radiation emitting pellets embedded in a plastic wire matrix 134, as shown in FIG. 7. The wire 132 is slidably attached within the lumen 136 of the shielding catheter 130 such that the wire 132 may slide in and out of the distal end of the shielding catheter 130. The shielding catheter 130 is constructed of such a shielding material 138 as to shield any radiation emissions while the active isotope wire 132 is contained within the shielding catheter 130. A syringe mechanism 140 is located at the proximal end of the shielding catheter 130 and has a movable plunger 142 that is connected to the proximal end of the active isotope wire 132. When the plunger 142 is withdrawn, the active isotope wire 132 is housed completely within the shielding catheter 130, as shown in FIG. 9. When the plunger 142 is depressed, the wire 132 extends from the distal end of the shielding catheter 130, as shown in FIG. 8. The distal end of the shielding catheter 130 is closed by a radiation proof valve 150. The radiation proof valve 150 acts to prevent any radiation leak out of the distal end of the shielding catheter 130 while still allowing the active isotope wire 132 to be moved in and out of the shielding catheter 130.

The large central lumen 112 of the double lumen catheter 110 is sized to receive the shielding catheter 130 within it. A locking mechanism 160 can also be provided to secure the shielding catheter 130 within the double lumen catheter 110 once the shielding catheter 130 has been fully inserted. A locking mechanism 170 can also be provided on the syringe mechanism 140 of the shielding catheter 130 to prevent accidental extension of the active isotope wire 132. Raised shoulders 180 can also be provided within the large central lumen 112 of the double lumen catheter 110. These shoulders 180 can act as brakes aiding in the full and proper insertion of the shielding catheter 130, as shown in FIG. 8. These shoulders 180 can be composed of a visualizable material, such as a radio opaque material, to aid in the proper positioning and targeting of the catheter system 100 and thereby aid in the targeting of the radiation delivery.

The outer double lumen catheter 110 can be disposable and designed for a single use only. The shielding catheter 130 can be used multiple times and can act as a storage container for the active isotope wire 132 between uses.

The present invention can also comprise a method of delivering radiation to an in vivo treatment site using a catheter. This embodiment of the present invention comprises the steps of inserting the catheter into the desired part of the body until it is properly positioned in vivo; delivering the radiation emitting isotopes through the catheter or unshielding the radiation emitting source within the catheter; allowing the radiation treatment to continue for the appropriate amount of time; and then removing and/or reshielding the radiation emitting source. The treatment time and frequency can easily be varied. The preferred frequency is a single treatment. The treatment time can be up to 30 to 40 minutes or even greater. Preferably, the treatment time is approximately 3–4 minutes. Placement of the radiation emitting material within the intravascular site can reduce the treatment time needed. Further, the placement of beta emitting isotopes closer to the vascular walls by delivering the isotopes through a peripheral coil wrapped around the inflatable balloon can reduce the treatment time needed and increase the effectiveness of the radiation treatment.

It should be understood, of course, that the foregoing relates only to preferred embodiments of the present invention and that numerous modifications or alterations may be made therein without departing from the spirit and the scope of the present invention as set forth in the appended claims.

What is claimed is:

1. A device for delivering radiation to an in vivo treatment site comprising:

an inner shielding catheter comprising a radiation shielded lumen and a radiation emitting portion comprising a radiation emitting material movable within the shielded lumen of the shielding catheter, wherein the radiation emitting material is axially slidable between a first configuration in which the radiation emitting material is contained within the shielded lumen and a second configuration in which the radiation emitting material extends from the distal end of the shielding catheter;

an outer catheter comprising at least a first lumen and a second lumen, wherein the first lumen is sized to receive the shielding catheter and the second lumen is capable of receiving a guide wire; and a radiation proof valve on the distal end of the shielded lumen.

2. The device of claim 1, wherein the radiation emitting material is a beta emitting isotope.

3. The device of claim 1, wherein the in vivo treatment site is an intravascular site.

4. The device of claim 1, wherein the outer catheter is disposable.

5. A device for delivering radiation to an in vivo treatment site comprising:

an inner shielding catheter comprising a radiation shielded lumen and a radiation emitting portion comprising a radiation emitting material movable within the shielded lumen of the shielding catheter, wherein the radiation emitting material is axially slidable between a first configuration in which the radiation emitting material is contained within the shielded lumen and a second configuration in which the radiation emitting material extends from the distal end of the shielding catheter;

an outer catheter comprising at least a first lumen and a second lumen, wherein the first lumen is sized to receive the shielding catheter and the second lumen is capable of receiving a guide wire; and a locking mechanism capable of selectively securing the shielding catheter within the outer catheter.

6. The device of claim 5, wherein the radiation emitting material is a beta emitting isotope.

7. The device of claim 5, wherein the in vivo treatment site is an intravascular site.

8. The device of claim 5, wherein the outer catheter is disposable.

9. A device for delivering radiation to an in vivo treatment site comprising:

an inner shielding catheter comprising a radiation shielded lumen and a radiation emitting portion comprising a radiation emitting material movable within the shielded lumen of the shielding catheter, wherein the radiation emitting material is axially slidable between a first configuration in which the radiation emitting material is contained within the shielded lumen and a second configuration in which the radiation emitting material extends from the distal end of the shielding catheter;

an outer catheter comprising at least a first lumen and a second lumen, wherein the first lumen is sized to receive the shielding catheter and the second lumen is capable of receiving a guide wire; and a locking mechanism capable of selectively preventing movement of the radiation emitting material.

10. The device of claim 9, wherein the radiation emitting material is a beta emitting isotope.

11. The device of claim 9, wherein the in vivo treatment site is an intravascular site.

12. The device of claim 9, wherein the outer catheter is disposable.

13. A device for delivering radiation to an in vivo treatment site comprising:

an inner shielding catheter comprising a radiation shielded lumen and a radiation emitting portion comprising a radiation emitting material movable within the shielded lumen of the shielding catheter, wherein the radiation emitting material is axially slidable between a first configuration in which the radiation emitting material is contained within the shielded lumen and a second configuration in which the radiation emitting material extends from the distal end of the shielding catheter;

an outer catheter comprising at least a first lumen and a second lumen, wherein the first lumen is sized to receive the shielding catheter and the second lumen is capable of receiving a guide wire; and a shoulder at the distal end of the outer catheter capable of stopping the insertion of the shielding catheter.

14. The device of claim 13, wherein the shoulders are observable in vivo.

15. A device for delivering radiation to an in vivo treatment site comprising a catheter having a proximal end and a distal end, further comprising:

a lumen for receiving a guidewire;

an inflatable balloon on the distal end of the catheter capable of immobilizing the distal end of the catheter at the treatment site when inflated;

an inflator channel in communication with the inflatable balloon;

and a radiation channel capable of delivering a radiation emitting material to the treatment site without releasing the radiation emitting material from the catheter, wherein the radiation channel is peripherally wound around the inflatable balloon.

16. The device of claim 15, wherein the radiation emitting material is a beta emitting isotope.

17. The device of claim 15, wherein the in vivo treatment site is an intravascular site.

18. A device for delivering radiation to an in vivo treatment site comprising a catheter having a proximal end and a distal end, further comprising:

a lumen for receiving a guidewire;

an inflatable balloon on the distal end of the catheter capable of immobilizing the distal end of the catheter at the treatment site when inflated;

an inflator channel in communication with the inflatable balloon;

a radiation channel capable of delivering a radiation emitting material to the treatment site without releasing the radiation emitting material from the catheter, and a return flow channel in communication with the radiation channel.

19. The device of claim 18, wherein the radiation emitting material is a beta emitting isotope.

20. The device of claim 18, wherein the in vivo treatment site is an intravascular site.

* * * * *